United States Patent
Adams et al.

(10) Patent No.: US 9,924,105 B2
(45) Date of Patent: Mar. 20, 2018

(54) SYSTEM AND METHOD FOR INDIVIDUALLY INSPECTING OBJECTS IN A STREAM OF PRODUCTS AND A SORTING APPARATUS COMPRISING SUCH SYSTEM

(71) Applicants: Dirk Adams, Tongeren (BE); Pieter Op de Beeck, Kortenaken (BE)

(72) Inventors: Dirk Adams, Tongeren (BE); Pieter Op de Beeck, Kortenaken (BE)

(73) Assignee: Visys NV, Hasselt (BE)

( * ) Notice: Subject to any disclaimer, the term of this patent is extended or adjusted under 35 U.S.C. 154(b) by 726 days.

(21) Appl. No.: 14/364,587

(22) PCT Filed: Dec. 11, 2012

(86) PCT No.: PCT/EP2012/075129
§ 371 (c)(1),
(2) Date: Jun. 11, 2014

(87) PCT Pub. No.: WO2013/087649
PCT Pub. Date: Jun. 20, 2013

(65) Prior Publication Data
US 2014/0333755 A1  Nov. 13, 2014

(30) Foreign Application Priority Data
Dec. 12, 2011  (EP) .................... 11193106

(51) Int. Cl.
*H04N 5/235*  (2006.01)
*G01N 21/85*  (2006.01)
(Continued)

(52) U.S. Cl.
CPC ........... *H04N 5/2353* (2013.01); *G01N 21/85* (2013.01); *G01N 21/8806* (2013.01);
(Continued)

(58) Field of Classification Search
CPC ........................ G06T 7/0004; H04N 5/2353
See application file for complete search history.

(56) References Cited

U.S. PATENT DOCUMENTS

| 4,634,881 A | 1/1987 | Billion |
| 4,723,659 A | 2/1988 | Billion |

(Continued)

FOREIGN PATENT DOCUMENTS

| EP | 0413522 A2 | 2/1991 |
| EP | 0552821 A2 | 7/1993 |

(Continued)

OTHER PUBLICATIONS

F. K. Chong et al.; "Optimization of Spinning Disk Confocal Microspy: Synchronization with the Ultra-Sensitive EMCCD"; Proceedings of SPIE vol. 5324; pp. 65-76; ISSN: 0277-786X.

*Primary Examiner* — Peter D Le
(74) *Attorney, Agent, or Firm* — Reinhart Boerner Van Deuren P.C.

(57) ABSTRACT

A system and a method for inspecting a stream of products (3, 3', 3") is disclosed, comprising a scanning focused light beam (5) for scanning the product stream and a camera (7) for detecting light beams directly returned from the scanned product stream, whereby the scanning movement of the focused light beam is synchronized with the exposure time of the camera.

19 Claims, 7 Drawing Sheets

(51) Int. Cl.
*G01N 21/88* (2006.01)
*G06T 7/00* (2017.01)
*G01N 21/89* (2006.01)

(52) U.S. Cl.
CPC ........ *G06T 7/0004* (2013.01); *G01N 21/8901* (2013.01); *G01N 2021/8838* (2013.01)

(56) References Cited

U.S. PATENT DOCUMENTS

| | | | | |
|---|---|---|---|---|
| 6,327,374 B1* | 12/2001 | Piironen | ............ | G01B 11/303 |
| | | | | 382/108 |
| 6,509,537 B1 | 1/2003 | Krieg et al. | | |
| 6,621,571 B1* | 9/2003 | Maeda | ............... | G01N 21/9501 |
| | | | | 356/237.4 |
| 2001/0043335 A1* | 11/2001 | Norita | .................... | G06T 7/521 |
| | | | | 356/601 |
| 2005/0093962 A1* | 5/2005 | Miyatake | ............. | G02B 26/123 |
| | | | | 347/235 |
| 2006/0064019 A1* | 3/2006 | Bush | .................. | G06K 15/1204 |
| | | | | 600/476 |
| 2008/0166140 A1* | 7/2008 | Noguchi | ................ | B41J 29/393 |
| | | | | 399/15 |
| 2010/0046826 A1* | 2/2010 | Dirix | .................... | B07C 5/3422 |
| | | | | 382/141 |
| 2011/0141270 A1* | 6/2011 | Miyake | ................ | G01N 21/896 |
| | | | | 348/125 |
| 2011/0292363 A1* | 12/2011 | Ivey | ........................ | G03F 7/703 |
| | | | | 355/55 |
| 2012/0097834 A1* | 4/2012 | Lin | .................... | G02B 13/0005 |
| | | | | 250/201.1 |

FOREIGN PATENT DOCUMENTS

| | | |
|---|---|---|
| EP | 1621914 A2 | 2/2006 |
| EP | 1724030 A2 | 11/2006 |
| EP | 1726372 A1 | 11/2006 |
| EP | 1332353 B1 | 12/2009 |
| WO | WO 2009/075580 A1 | 6/2009 |

* cited by examiner

SYSTEM AND METHOD FOR INDIVIDUALLY INSPECTING OBJECTS IN A STREAM OF PRODUCTS AND A SORTING APPARATUS COMPRISING SUCH SYSTEM

FIELD OF THE INVENTION

The present disclosure relates to a system and a method for inspecting individual objects in a continuous stream of products. The present disclosure also relates to an apparatus for sorting products using such an inspecting system.

STATE OF THE ART

An apparatus for sorting products provided in a continuous stream is known in the art. Such sorting apparatus comprises a transport system, an inspection system and a removal system. The transport system conveys the product stream to be inspected towards the inspection system and the removal system. The inspection system will analyze one or more predetermined characteristics of the products. Typically optical characteristics such as color and structure are being examined. Based upon the optical signals it receives, the inspection system will evaluate if the measured values of these characteristics for a given object in the product stream meet predetermined acceptance criteria. If not, this object is subsequently removed from the product stream by the removal system. Hereto the inspection system controls the operation of the removal system.

The configuration of such a sorting apparatus is disclosed by U.S. Pat. No. 6,509,537. This sorting apparatus comprises a conveyor belt as transport system for transporting a stream of solid particles, and a device for detecting and differentiating between the quality and/or the color of the individual solid particles. The detection system comprises a laser beam, which is redirected towards the solid particles via a polygon wheel. Due to the rotation of the polygonal wheel, the mirroring end surfaces of the wheel will azimuthally guide the laser beam in a temporal saw-tooth movement. The moving laser beam is then directed towards the stream of solid particles to provide a linear laser beam scan thereof. The light, which is reflected by the solid particles, is partly redirected via the mirroring end surfaces of the polygonal wheel towards photoelectrical devices converting the optical signal into an electronic output signal. This output signal can then be further handled by analog electronic circuitry or converted into a digital signal for digital processing and data manipulation.

Likewise U.S. Pat. No. 4,723,659, U.S. Pat. No. 4,634,881 and European patent EP 1 332 353B1 disclose sorting devices comprising inspection systems using laser light.

SUMMARY OF THE INVENTION

There is a need for an inspection system that allows inspection of individual products provided in a continuous stream whereby inspection of an individual product is not jeopardized by neighbouring products. Such an inspection system should allow identifying inspected products by analysing the light, which has been reflected by the inspected product, based at least on wavelength. Such an inspection system should be configured at minimal cost.

There is a need for an inspection system that allows inspection of individual products provided in a continuous stream using a scanning focused light beam which has improved radiant efficiency at the point of inspection.

There is a need for an inspection system that allows inspection of individual products provided in a continuous stream using a scanning focused light beam and allows analyses of the scanned products over a broader spectral range without cumbersome and/or costly reconfigurations.

There is a need for an inspection system that allows inspection of individual products provided in a continuous stream using a scanning focused light beam with a very narrow spectral bandwidth.

The invention as presently disclosed answers to these needs. The invention is related to systems, methods and apparatuses as disclosed in the appended claims.

In a first aspect the disclosure is related to an inspection system for individually analyzing products provided in a continuous stream, the system comprising a scanning focused light beam source, configured to scan the width of the product stream in a period of time referred to as the scan time $T_w$, a camera positioned to detect light beams directly returned from the scanned product stream in a period of time referred to as the exposure time $T_e$ of the camera, thereby providing an image of the scanned product stream, and a control unit configured to synchronize the scanning of the focused light beam with the exposure time of the camera.

The scanning of the focusing light beam with the exposure time of the camera can be synchronized by synchronizing the number of scans performed within the exposure time.

Preferably, synchronizing comprises configuring the exposure time and the scan time so that the exposure time $(T_e)$ is substantially equal to an integer ratio of the scan time $(T_w)$. This is the case for example when one or more subsequent exposure times $T_e$ are processed, the total exposure time equalling an integer number K of exposure times $T_e$ and the total scan time equalling an integer number L of scan times $T_w$, when $K \times T_e$ is substantially equal to $L \times T_w$ (with $K \geq 1$ and $L \geq 1$).

Preferably the number of scans to be performed is determined such that the exposure time is an integer multiple of the scan time, the integer being one or higher.

This inspection system can further comprise at least one start sensor positioned with respect to the light source to define the angle over which the focused light beam moves when scanning the product stream, whereby the sensor is configured to provide a control signal to the control unit indicative of the start of a scan movement of the focused light beam.

This inspection system can further comprise two sensors, respectively a start sensor and stop sensor positioned with respect to the light source to define the angle over which the focused light beam moves when scanning the product stream, whereby the start sensor and the stop sensor are configured to provide a control signal to the control unit indicative of respectively the start and the stop of a scan movement of the focused light beam.

In a second aspect the disclosure relates to a method for operating an inspection system according to the first aspect, the method comprising: initiating scanning of the product stream thereby generating a signal to the control unit to start recording the number of scans being performed and to the camera to start integrating the light returned by the scanned products towards the camera, checking if the number of scans performed corresponds to an integer multiple of the scan time, and if so, instructing the camera to stop detecting the returned light and processing the image or images taken.

In a third aspect the disclosure relates to an apparatus for sorting products, comprising a transport system configured to supply the products in a continuous single layer stream to an inspection system which is positioned towards the product stream to allow analysis of individual products and a removal system operatively coupled to the inspection system to remove products analyzed by the inspection system, wherein the inspection system is according to the first aspect and can be operated according to the second aspect.

In a fourth aspect the disclosure relates to a method for operating the sorting apparatus according to the third aspect. The method comprises: providing the product stream, initiating scanning of the product stream thereby generating a signal to the control unit to start recording the number of scans being performed and to the camera to start integrating the light returned by the scanned products towards the camera, checking if the number of scans performed corresponds to an integer multiple of the scan time, and if so, instructing the camera to stop detecting the returned light and processing the image or images taken, and on the basis of said processing, analyzing and if necessary removing individual products from said product stream.

TABLE 1

Figure 1:
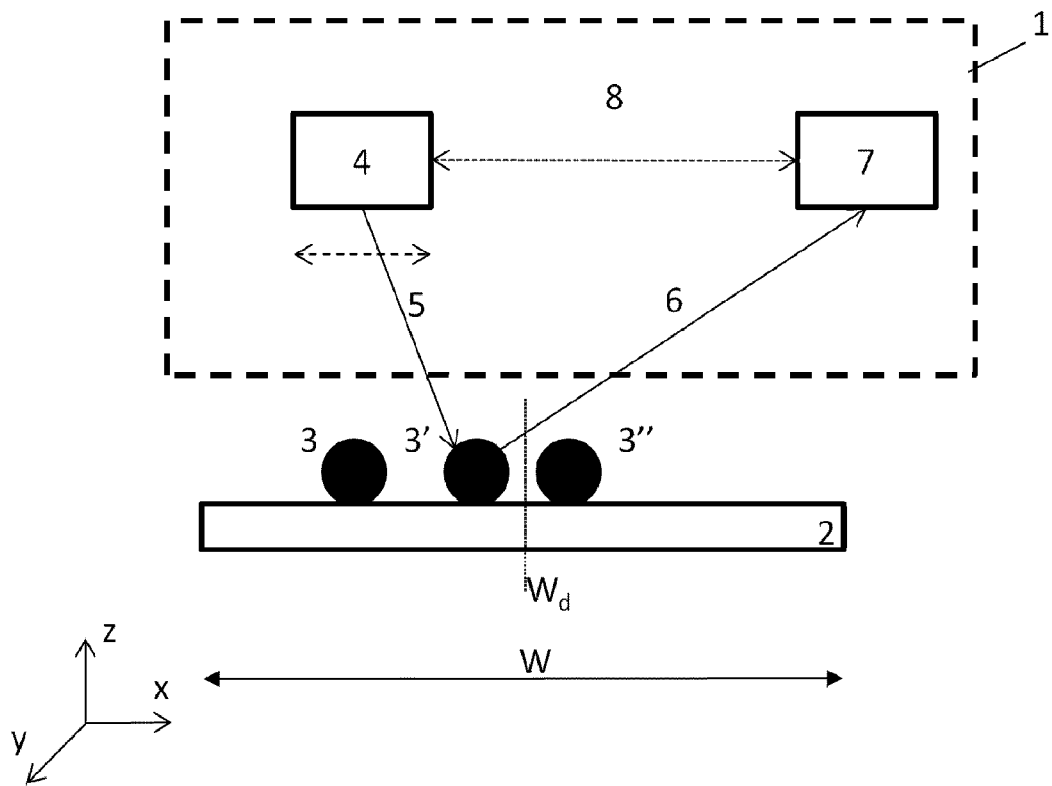
FIG. 1 illustrates an inspection system according to this disclosure.

| Nr | Description |
|---|---|
| W | Width of the product stream |
| 1 | inspection system |
| 2 | transport system |
| 3, 3', 3" | products |
| 4 | source providing a scanning focused light beam |
| 5 | focused light beam |
| 6 | light returned from scanned products 3, 3', 3" |
| 7 | camera |
| 8 | synchronization of scanning focused light beam 4 and exposure time of camera 7 |
| 9 | pixel of the camera 7 |
| 10 | start sensor |
| 11 | stop sensor |
| 12 | control unit |
| 13 | sorting apparatus |
| 14 | removal system |
| 15 | rejected product |
| 16 | laser source |

TABLE 1-continued

| Nr | Description |
|---|---|
| 17 | rotatable polygon mirror |
| 18 | light returned to mirror 17 |
| 19 | semi-transparent mirror |
| 20 | detector |
| 21, 21' | electronic output signals from camera 7 and detector 20 |
| 22 | control signal to removal system 14 |

DETAILED DESCRIPTION OF THE INVENTION

The present invention will be described with respect to exemplary embodiments and with reference to certain drawings but the invention is not limited thereto. The drawings described are only schematic and are non-limiting. In the drawings, the size of some of the elements may be exaggerated and not drawn on scale for illustrative purposes. Hence the dimensions and the relative dimensions do not necessarily correspond to actual reduction to practice of the invention. It is intended that the embodiments and figures disclosed herein be considered illustrative rather than restrictive.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein. For example "underneath" and "above" an element indicates being located at opposite sides of this element.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. Like elements are referred using like numerals. The mere fact that certain measures are recited in mutually different dependent claims does not indicate that a combination of these measures cannot be used to advantage.

Embodiments disclose an inspection system 1 comprising a scanning means 4 and a detecting means 7. An inspection system 1 according to these embodiments is of particular use in an apparatus 13 (see FIG. 9) for sorting products 3 which are supplied in a continuous single layered stream, as disclosed in a third aspect. Such a sorting system 13 is used for inspecting and sorting particular granular products, e.g. in the food industry such as raisins, blueberries, rice, nuts, dried fruits, frozen vegetables and such like or in the recycling industry such as electronic waste, glass fragments, plastics and such like, but also pellets e.g. plastic pellets or wood, flakes, etc. Such a sorting system is also used for inspecting planar products such as glass plates, e.g. windows. In such a continuous sorting process the inspection process is not interrupted by the removal process.

A system 1 for inspecting a stream of products 3 is disclosed. The inspection system 1 comprises a means for producing a scanning focused light beam 5 scanning the product stream 3 and a camera 7 detecting light beams 6 directly returned from the scanned product stream 3, whereby the scan time $T_w$ of the focused light beam 5 is synchronized with the exposure time $T_e$ of the camera 7. In the present description, the 'scan time or period $T_w$' is defined as the time taken up by one single scan movement over the width W of the product stream. The 'exposure time Te' is the time taken up by one single data acquisition by the camera, e.g. the time taken up for receiving the reflected light data from a predefined number of points along the width W. The 'total scan time' corresponds to an integer number (one or more) of scan times $T_w$. The 'total exposure time' corresponds to an integer number (one or more) of exposure times $T_e$.

Such an inspection system 1 is illustrated by FIG. 1. A transport system 2 conveys products 3, 3', 3" to be inspected towards an inspection zone. When in the inspection zone, these products 3, 3', 3" are scanned by the focused light beam 5 provided by a light source 4. The focused light beam 5 scans the width W of the product stream along a scan line. The width W of the product stream is the linear dimension of the product stream in a direction x substantially perpendicular to the direction y along which the product stream is transported by the transport system 2. Light 6 returned by the product being scanned is collected by a camera 7. As this camera 7 is oriented towards the products 3, 3', 3", the scanned product is within line of sight of the camera 7 and the returned light 6 is directly received by the camera 7. The spot size of the focused light beam 5, at least along the width of the product stream, is substantially smaller than the width W of the product stream. Typically this spot size is in the order of one millimeter or less, whereas the width W is in the order of meters, typically between 0.5 meters and 3 meters. Preferably the products 3 are spread out over the width of the transport system 2 allowing a maximal throughput of the inspection system 1.

Figure 2:
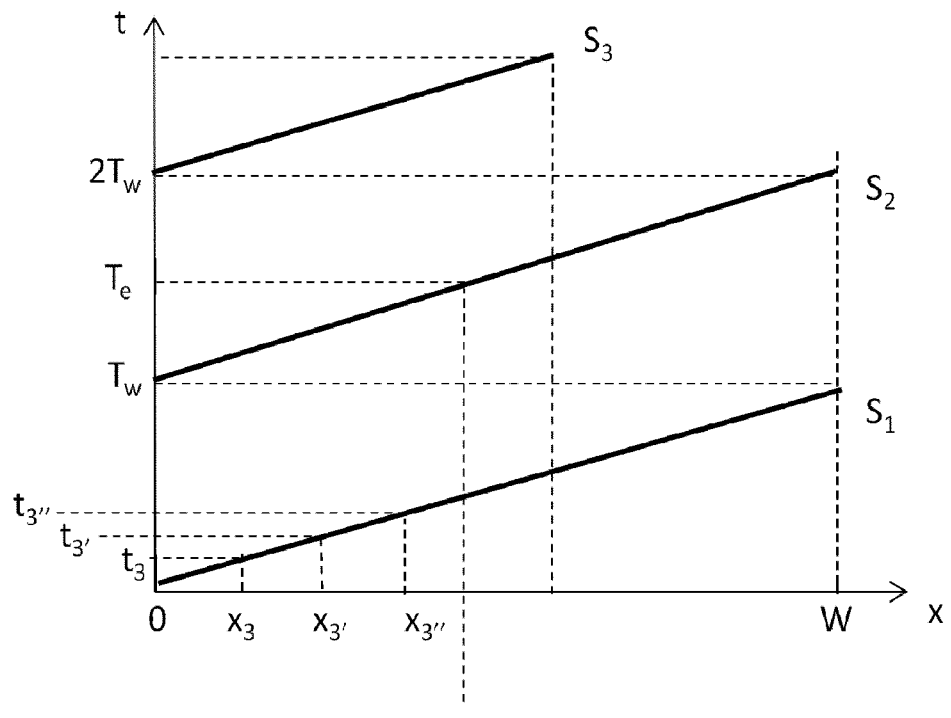
FIG. 2 illustrates the temporal saw-tooth movement of the focused light beam when scanning the product stream according to this disclosure.

The operation of this inspection system is illustrated by FIG. 2. The focused light beam 5 moves during a scan period $T_w$ over the width W of the product stream entering the inspection zone, i.e. the area scanned by the focused light beam 5, such that during this scan period $T_w$, the width W of product stream is scanned once. Typically the scanning is performed in a temporal saw-tooth movement. In FIG. 2 two complete scans $S_1$, $S_2$ were performed, while the focused light beam 5 is performing a third scan $S_3$. The focused light beam 5 scans the product stream several times per second. The higher this linear scan rate $\sigma=1/T_w$ (number of scans/second or Hz), the more scans are performed in one second. The speed $V_1$ at which the focused light beam 5 moves over the width W of the product stream is $V_1=\sigma \cdot W$ (m/s). For example, when the scan rate $\sigma$ is 4000 scans per second over a width W of 1.2 meters, the resulting focused light beam 5 moves at a speed $V_1$ equal to 4800 m/s (or 17280 km/h). Typical scan rates range from 1000 scans per second up to 12000 scans per second although the current invention is not limited to said typical range.

Figure 3:
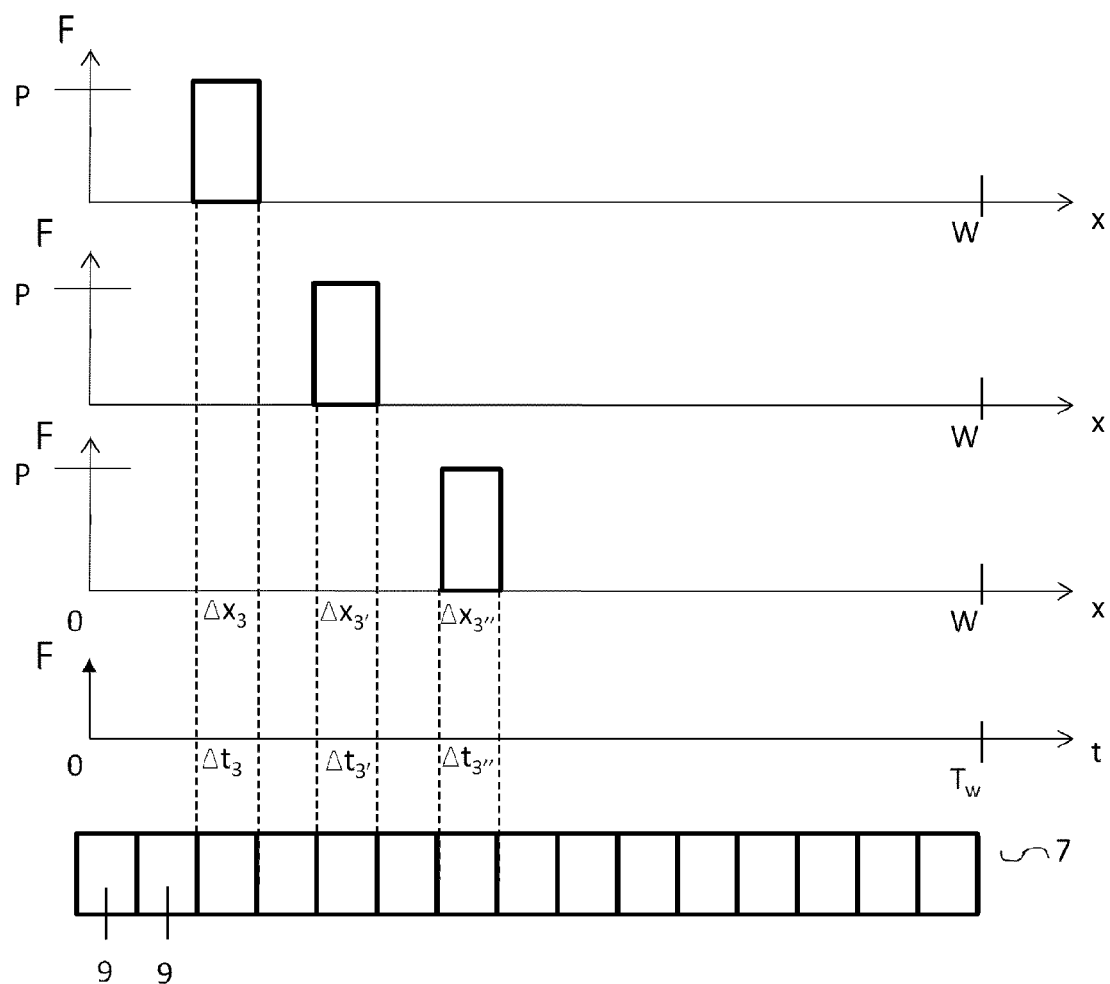
FIG. 3 illustrates the successive scanning of products along the width of the product stream according to this disclosure.

As illustrated by FIG. 3, the focused light beam 5 will successively illuminate products 3, 3', 3" positioned along the width of the product stream. As the scanning light beam 5 is focused, each product 3, 3', 3" will be illuminated with the same maximal radiant flux F provided by the light source 4 such that an improved radiant efficiency is achieved compared to the case of uniform or diffuse illumination of the product stream using, for instance, a TL-tube. At moment $t_3$ product 3 will receive substantially all of the radiant flux F of the focused light beam while other products 3', 3" in the product stream are essentially not illuminated. Next, at moment $t_{3'}$ product 3' will receive substantially all of the radiant flux F of the focused light beam while other products 3, 3" in the product stream are essentially not illuminated. Next, at moment $t_{3''}$ product 3" will receive substantially all of the radiant flux F of the focused light beam 5 while other products 3, 3' in the product stream are essentially not illuminated. This is illustrated by the 3 upper curves in FIG. 3 giving the radiant flux F in a particular section $\Delta x_i$ along the width of the product stream during a given delta time $\Delta t_i$. The bottom curve in FIG. 3 illustrates how a particular $\Delta x_i$ corresponds to a particular $\Delta t_i$ during the scanning of the width W of the product stream.

Light 6 returned from the scanned products is directly received, i.e. without being reflected or handled by the scanning light source 4, by a camera 7 comprising at least one line of photosensitive elements 9. Each product 3, 3', 3" essentially only receives energy from the focused light beam 5 during a small fraction of the scan period $T_w$, i.e. when the focused light beam 5 is directed towards that particular section $\Delta x_i$ along the width W of the product stream. During each $\Delta t_i$ of the scan period $T_w$, the light received by the camera 7 will hence be representative for the irradiated power from the particular product at $\Delta x_i$. The products not illuminated by the focused light beam 5 will return essentially no light to the camera 7. Each pixel 9 in a line of sensors of the camera 7 is allocated to a particular section $\Delta x_i$ along the width W of the product stream.

The exposure time $T_e$ is the time needed by the camera 7 to make (or integrate) and read-out one image of the scanned product stream at the inspection zone. The smaller this exposure time $T_e$, the more images can be taken in one second. The frame rate $\Phi$ (number of images or in case of line-scan sensors, number of lines, per second or Hz) is inverse proportional to the exposure time $T_e$ (s).

The required number of frames per second $\Phi_{req}$ to capture said concentrated light beam 5 moving at speed $V_1$ across the width W of the product stream with a resolution $r_w$ along said direction x across the width of said product stream, equals $V_1/r_w$. For example, when a resolution $r_w$ of 1 mm ($r_w=0.001$ meter) is required, which would not be uncommon, and the focused light beam 5 is travelling at a speed $V_1=4800$ meters per second, again not uncommon, then the required frame rate $\Phi_{req}$ would have to be 4.8 million frames per second. Imaging systems capable of such high frame rates are infeasible in practice because, amongst other things, they would be too expensive to deploy in industrial inspection and/or sorting machines.

Typically imaging systems have an exposure time $T_e$ that is higher but in the same order of magnitude than the scan period $T_w$. For instance, an exposure time $T_e$ of 1/20000 seconds (or $\Phi=20000$ frames per second) is not uncommon for standard 2048 pixel line-scan cameras. The current invention applies to any frame rate $\Phi$ and any scan rate $\sigma$ and any combination thereof.

It was surprisingly discovered that an interesting case occurs when the frame rate $\Phi$ is actually smaller than the scan rate $\sigma$ ($\Phi<\sigma$), in other words $T_w<T_e$. In this situation each product is scanned more than once during said exposure time $T_e$. In fact the inspection zone can be divided into a first section with range $[0, W_d]$ and a second section with range $[W_d, W]$ which second section has been scanned one time less than said first section such that objects 3, 3' in said first section are exposed 2 times to said concentrated light beam 5 and objects 3" in said second section are exposed 1 time. In general said first section will be N+1 times exposed to said concentrated light beam 5 and said second section will be exposed N times. FIG. 2 shows the situation where N=1. The maximum point $W_d$ of said first section is computed in general as $W_d = W(T_e - NT_w)/T_w$.

If different products 3, 3', 3" are scanned a different number of times during the exposure time $T_e$ of said camera 7, the accumulated energy of the returned light 6 may vary from one product to another, even if these products are alike. The relative exposure time error $E_{exp}$ between objects 3,3' in said first section $[0, W_d]$ and said second section $[W_d, W]$ is N/(N+1), where N is the number of times said second section has been exposed. To minimise said relative exposure error $E_{exp}$, N should be as high as possible. This could be achieved by having an exposure time $T_e$ which is substantially larger than said scan time $T_w$.

Typically however said exposure time $T_e$ is bound by the required resolution $r_t$ in said direction y, the direction of travel of said product stream. If said product stream travels at a speed $V_s$, then said resolution $r_t$ is calculated as $V_s T_e$. For instance, if $V_s = 3$ meters per second and $r_t$ is required or specified to be 1 mm, then $T_e$ would have to be 0.001/3=0.0003 seconds, which corresponds to a frame rate $\Phi$ equal to 3000 frames per second.

This invention relates to the problem that occurs when said exposure time $T_e$ and said scan time $T_w$ are such that said exposure error $E_{exp}$ cannot be neglected in the sense that the accumulated energy of the returned light 6 may vary from one product to another, even if these products are alike.

As illustrated by FIG. 1 the scanning focused light beam 5 is synchronized 8 with the camera 7. Synchronization of illumination and detection allows correctly identifying the inspected products by analysing the returned light. The start/stop of the scanning, i.e. the total scan time is synchronized with the exposure time $T_e$. In other words, the total scan time starts and stops at predefined moments in time with respect to the exposure time. This way, a known correlation between the exposure time and the total scan time can be exploited: for each point of the scanned width (W), the number of exposures to the scanning beam is known in advance, and can thus be taken into account when the information contained in the reflected light is processed. This correlation of the scanning of the product stream with the registration of the returned light can take into account and compensate for known variations on the scanning speed and phase.

Preferably, the exposure time $T_e$ is substantially equal to an integer ratio of the scan time $T_w$ of one single scan along the width W. In other words, $T_e$ equals $(n/m)*T_w$ with n and m being integers ($n \geq 1$ and $m \geq 1$). For example, when $T_e$ equals $(3/2)*T_w$, and the control unit is configured (by a suitable start sensor, see further) to start the camera exposure simultaneously with a first scan, one integration will take 1.5 scans. The total amount of scans cannot be chosen to be a non-integer number, so in this case, at least two scans are required for one image of the width to be processed. In the image taken by the camera, one half of the width is scanned twice. As this is known in advance, it can be taken into account in the processing of the returned light. More preferably however, more than one exposure time is processed in sequence, and the data of each exposure time are added together.

In the example, two exposure times correspond to three scan times, so when the product width is scanned three times and the two exposure times are added together, each point in the width has been exposed twice. In general, when $T_e$ equals $(L/K)*T_w$, K exposure times ($K \times T_e$) is equal to L scan times ($L \times T_w$). In other words, when the data of K subsequent exposure times are added together, these data are known to correspond to the situation where each point along the width W is exposed L times to the scanning beam. In other words, the number of scans L and the number of subsequent exposures are preferably chosen so that the total exposure time (i.e. $K \times T_e$) equals an integer number L of scan times $T_w$.

It is to be noted that the invention is not limited to the case where $T_e > T_w$. For example, when $T_e = (2/3)*T_w$, one exposure time is insufficient to analyse the complete width W. However, two scans correspond to exactly three exposure times. When the data of three subsequent exposure times are added together, these data are known to correspond to the situation where each point along the width W is exposed twice to the scanning beam. So once again, the number of scans and exposures is preferably chosen so that the total exposure time (i.e. $(3 \times T_e)$) equals an integer number of scan times $T_w$ ($2 \times T_w$).

The most preferred case is the one wherein the exposure time $T_e$ is an integer multiple of the scan time $T_w$ of a single scan (i.e. $T_e = n*T_w$ with $n \geq 1$). In other words, the scan rate $\sigma$ is an integer multiple $n \geq 1$ of the frame rate $\Phi$ or mathematically ($\sigma \mod \Phi$)=0. In such a synchronization set-up, the camera 7 starts registering the returned light 6 at the start of the scan movement, or after a predetermined time period from the start of the scan movement, and stops registering the returned light 6 when the focused light beam 5 has scanned the width W of the product stream one or several times ($n \cdot T_w$), whereby the total scan time ($n \cdot T_w$) is equal to the exposure time $T_e$ of the camera 7. Now we find that the exposure error $E_{exp}$ is zero and the accumulated energy of the returned light 6 coming from objects 3,3' and 3" at any position in the inspection zone can be analyzed in a deterministic way such that like objects generate like results.

According to a further preferred embodiment, the exposure time Te for obtaining one read-out signal is an integer number n of scan times Tw with n at least equal to 2. In this way, each read-out operation (concluded at the end of each single exposure time Te) results in a signal that is the (analogue) integration of multiple signals, corresponding to the same points along the scanned line. This allows to obtain a high signal to noise ratio in the final image, as the total attributed noise predominantly originates from the read-out mechanism and will therefore decrease with increasing n. This is because a higher value of n means that a higher number of signals are integrated at the end of each exposure time, and fewer total read-outs are required for obtaining a good image of the products. The measurement thus obtained becomes comparable to images obtained by complex, expensive and powerful lighting and camera systems with very short exposure times, which are capable of measuring each point along the scanned line individually. The difference is that the system of the invention does not require such expensive systems while still ensuring a high quality detection.

Figure 4:
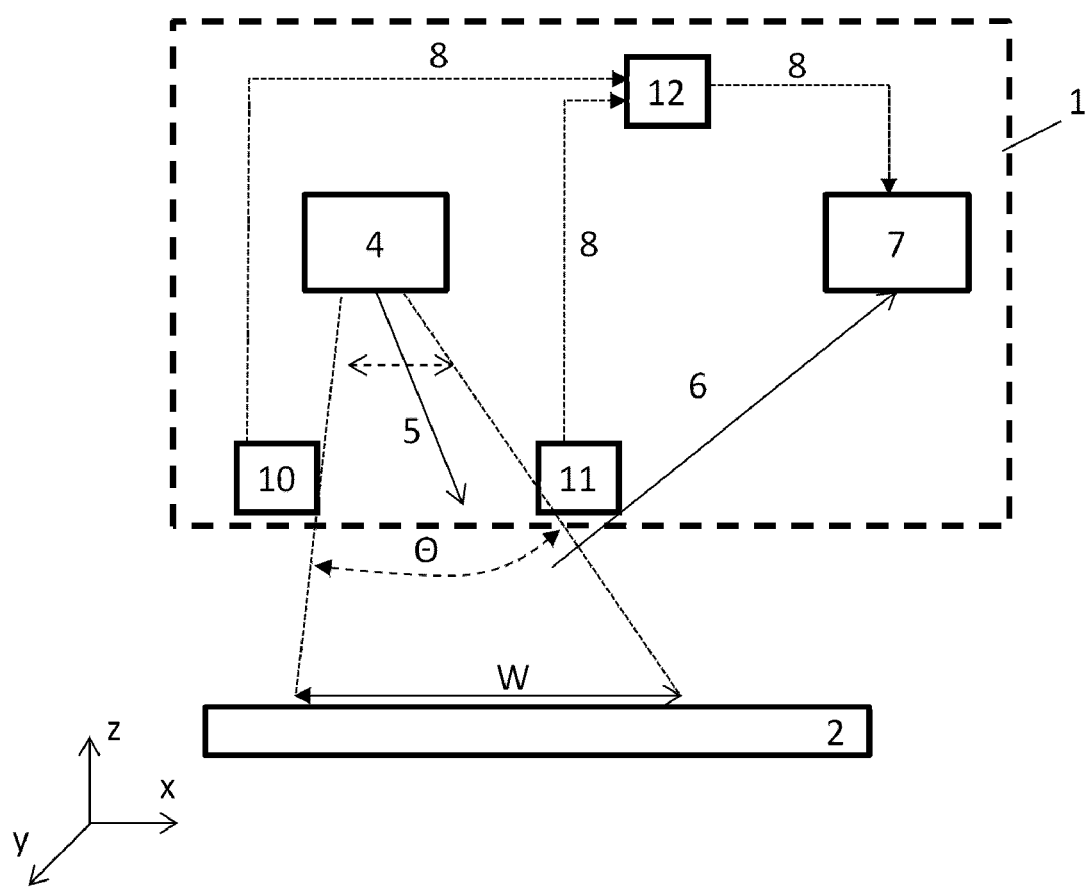
FIG. 4 illustrates another inspection system according to this disclosure.

FIG. 4 shows an example of how the scanning and detection can be synchronized. The inspection system 1 further comprises a start sensor 10 and a stop sensor 11. Both sensors 10 and 11 are positioned with respect to the light source 4 such that they define the angle θ over which the focused light beam 5 moves when scanning the width W of the product stream. Start sensor 10 detects the start of the scan movement. For example, if an opto-electronic device is used as start sensor 10, an electronic start signal is created when the focused light beam 5 strikes this device 10 before striking the product stream. Stop sensor 11 detects the end of a scan movement. If, for example, an opto-electronic device is used as stop sensor 11, an electronic stop signal is created when the focused light beam 5 strikes this device 11 after completing its sweep θ over the width W of the product stream. The inspection system 1 further comprises a control unit 12 controlling the synchronization of the exposure time with the number L of scans. Hence the source 4 providing the scanning focused light beam 5 and the camera 7 are operatively 8 linked. In a preferable embodiment only 1 sensor can be used, to detect the start of the scan movement triggering the start of the registration of the returned light or, mutatis mutandis, to detect the stop of the scan movement triggering the stop of the registration of the returned light.

The start sensor 10 and/or stop sensor 11 can be constructed using a photo diode sensitive to at least one wavelength of said concentrated light beam 5. The person skilled in the art will however appreciate that any opto-electrical device can be used as start and/or stop sensor as long as it is capable of generating a signal indicating the start and/or stop of said scan movement.

Figure 5:
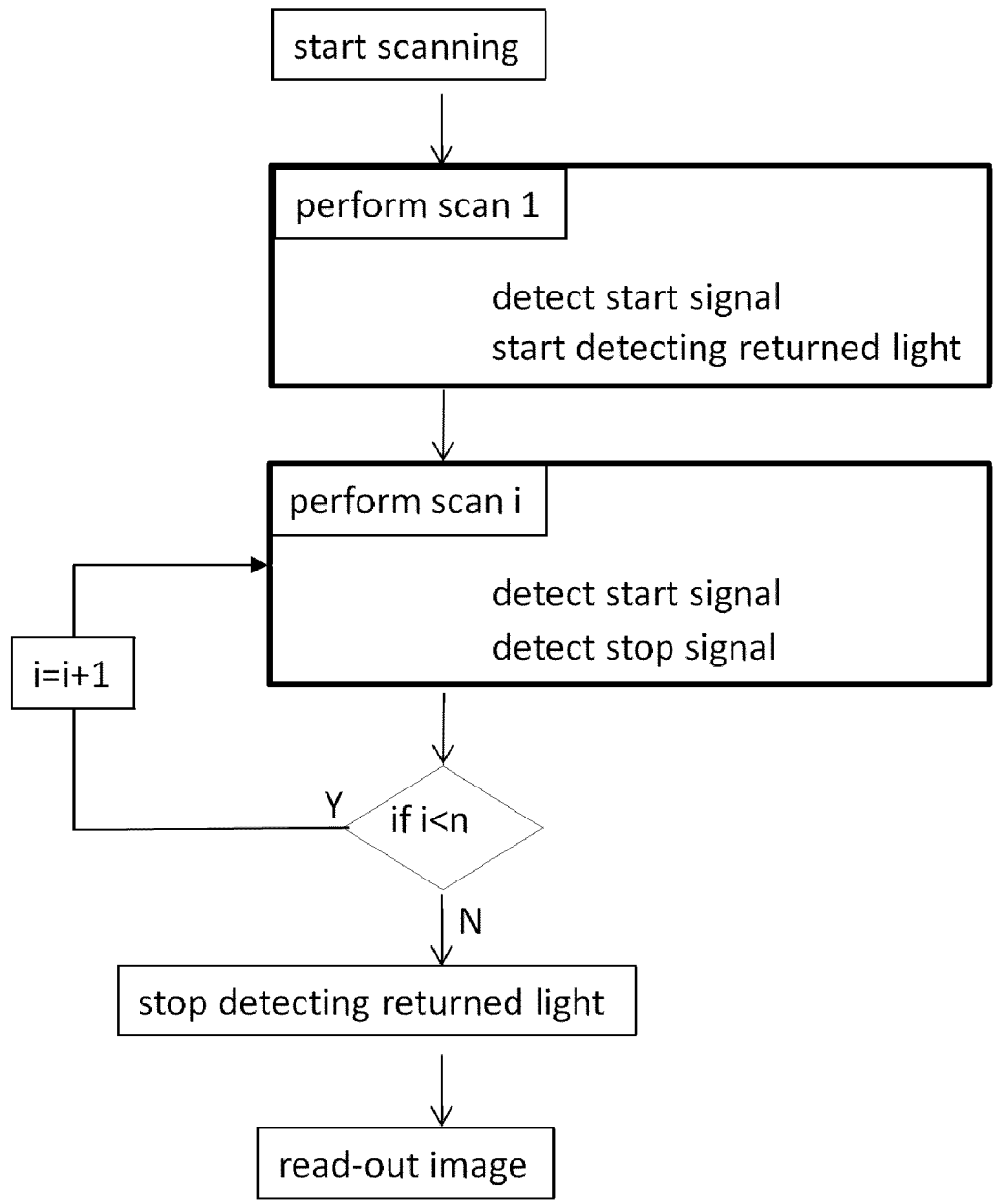
FIG. 5 shows a flow chart illustrating the operation of an inspection system according to this disclosure.

FIG. 5 illustrates the operation of an inspection system 1 as illustrated in FIG. 4. The start signal generated by the start sensor 10 is input to this control unit 12 upon which event the control unit 12 triggers the camera 7 to start detecting the returned light 6. The camera 7 starts integrating over time the optical information 6 received. The control unit 12 records the number i of scans performed. When the total scan time (n×Tw) is at equal to the exposure time $T_e$ of the camera 7, the control unit 12 instructs, upon receipt of the corresponding stop signal from the stop sensor 11, the camera 7 to stop detecting the returned light 6 and to read-out the image taken. One can select any integer value for the number n of scans to be performed when taking an image of the scanned product stream. After reading-out the image taken, this image can be analyzed to determine optical properties of the scanned products 3. Upon this analysis the scanned products can be sorted into at least two product streams. The above corresponds to the case where the exposure time $T_e$ of the camera (the taking of one image) is an integer multiple of the scan time Tw, hence Te=n×Tw with n higher than or equal to 1. A more preferred case is the one where n is equal to or higher than 2, for reasons of signal to noise ratio, explained above. In both cases (n≥1 and n≥2), the camera may take multiple images taken over multiple exposure times, which are read out and added together in the camera or in a processing device outside the camera. In a more general case, the exposure time is chosen so that K×Te equals L×Tw with L and K integers higher than or equal to 1. In that case, when the total exposure time equals an integer number K of exposure times $T_e$, the camera is instructed to stop detecting the returned light at the end of the period $L*T_w$, which is equal to $K*T_e$, and the subsequent K images are integrated (added) in the camera or in a processing device separate from the camera. The most general case is the one where the exposure time Te is an integer ratio n/m of the scan time, wherein the exposure time is started upon receiving a signal that the scanning is initiated, and wherein after detecting that an integer number of scan times have been applied, the data obtained during the exposure time is read out and processed. In this case, one exposure time may correspond for example to 1.5 time the scan time (as in the example explained elsewhere in this description). Even though not all the points in the detection area have then received the same amount of light during the exposure time, the knowledge that one half of the points have obtained twice the amount of the other half, allows the processing means to analyse the data taking this knowledge into account.

In an alternative method the start and stop signals are taken from the same sensor 10 such that the start of the current exposure period coincides with the stop of the previous exposure period.

Figure 6:
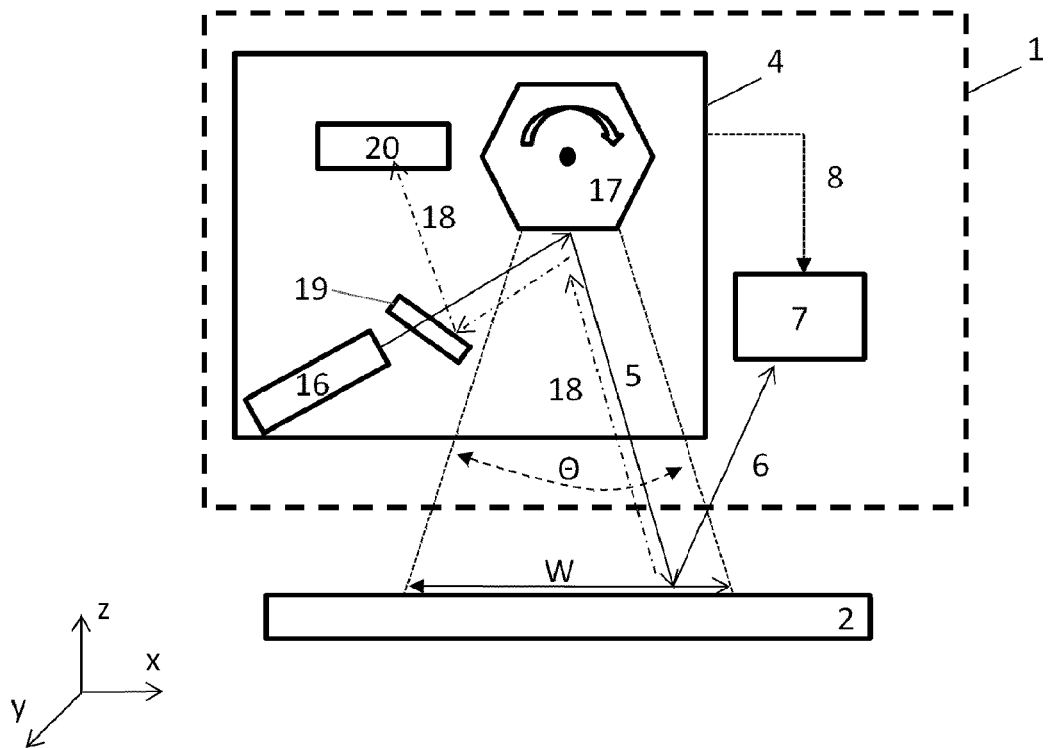
FIG. 6 illustrates another inspection system according to this disclosure.

FIG. 6 shows another example of an inspection system 1 according to this disclosure. The detection system comprises at least one light source 4 for generating a scanning focused light beam 5, the light beam 5 having (a) predetermined wavelength(s) which is (are) chosen in function of the product 3 to be analyzed as is known in the art, and a camera 7 which is operatively 8 linked with the light source 4, e.g. by a start and/or stop sensor, thereby synchronizing the exposure time of the camera with the number of scans performed by the scanning focused light beam 5. The light source 4 further comprises at least one laser source 16 generating a laser beam 5 whereby the laser beam 5 comprises radiation at at least one wavelength. In operation, this laser beam 5 is guided via a rotating polygonal mirror 17 over the product stream such that the light beam 5 scans over an angular range θ at least comprising the product stream. The irradiating product will return light beams 6,18 characteristic for the product. The irradiated light will typically be of a diverging nature. Part 18 of the returned light will be reflected by the rotating polygonal mirror 17 and an optical system 19, e.g. a semi-transparent mirror, to an opto-electronic device 20, such as a photodiode or photomultiplier. The light beam 18 incident on the photoelectrical device 20 is converted by this device in an electrical output signal characteristic for the product from which this light beam 18 stems. In particular the spatial distribution of the returned light, i.e. scattering and/or specular and/or diffuse reflection, can be determined using this portion 18 of the returned light. Also this signal is processed to determine whether or not this product passes the selection requirements. Part 6 of the returned light will be detected, as discussed in the foregoing paragraphs, by the camera 7 in order to take an image of the scanned product stream.

In an alternative to the embodiment illustrated by FIG. 6, the start and/or stop sensor is selected such that it can measure the rotation of the rotating polygonal mirror 17. For example, the start and/or stop sensor can be a HAL sensor detecting the position of the magnetic field of the electrical motor driving the rotating polygonal mirror 17. The person skilled in the art will immediately understand that any type of rotary encoding device operatively connected to the rotating polygonal mirror 17 can be used as a start and/or stop sensor according to the invention.

Figure 7:
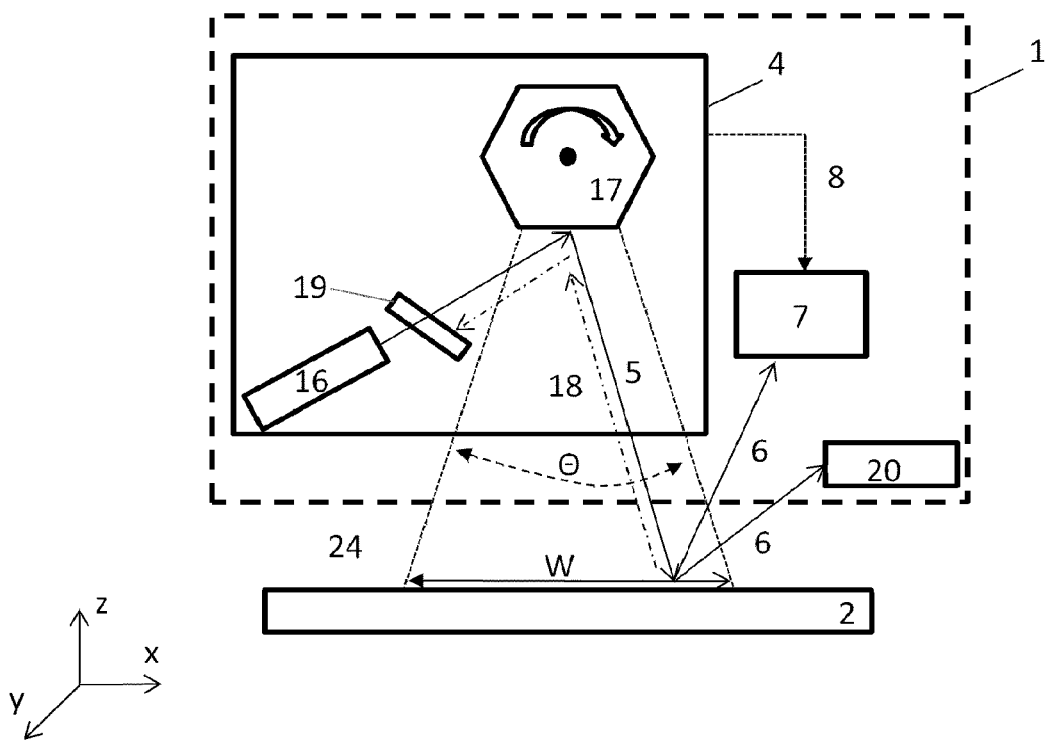
FIG. 7 illustrates another inspection system according to this disclosure.

In an alternative to the embodiment illustrated by FIG. 6, the position of the photoelectrical device 20 is selected to allow light returning from the scanned products 3 to incident directly on the photoelectrical device 20 as shown in FIG. 7. The returned light beam 6 need not to be reflected by the rotating polygonal mirror 17 towards the photoelectrical device 20. Hence the design of this mirror 17 can be simplified, e.g. by reducing the dimensions of the reflecting sidewalls thereof resulting in a smaller, hence cheaper and more reliable mirror 17.

Figure 8:
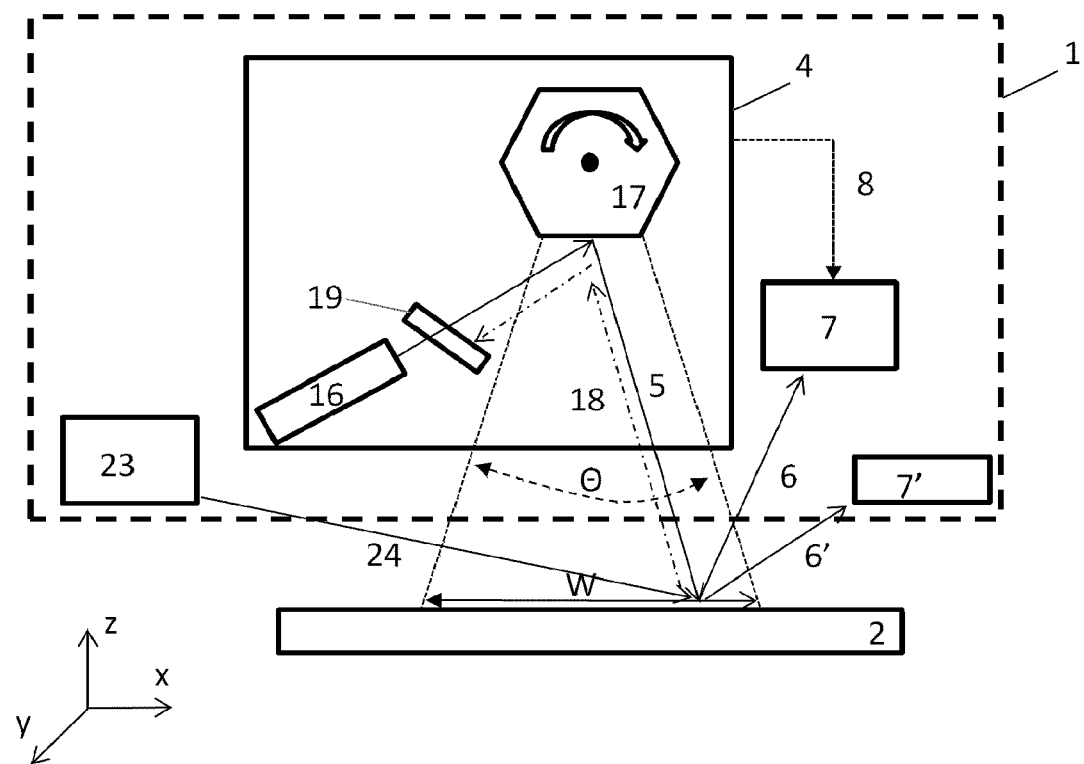
FIG. 8 illustrates another inspection system according to this disclosure.

In an alternative to the embodiment illustrated in FIG. 6, 2 camera's 7, 7' can be used as illustrated by FIG. 8. A first camera 7 is configured to receive light 6 returned from the product stream 3 upon scanning by the scanning focused light beam 5. As disclosed in the foregoing paragraphs the scanning of the product stream 3 is synchronized with the registration of the returned light by the first camera 7. A second light source 23 is provided which illuminates 24 the product stream 3 uniformly (i.e. diffuse) over its width W. The wavelength of the light 24 provided by this second light source 23 is typically selected to be outside the detection range of the first camera 7. The second camera 7' is sensitive for the wavelength of the light 24 provided by this second light source 23, but typically not for the wavelength of the scanning focused light beam 5 provided by the first light source 4. This second camera 7' is positioned to receive light from the second light source 23 which is returned 6' by the illuminated products 3.

This invention is not limited to embodiments with one or two cameras but any number of cameras can be combined if the application would require such as setup as will be well understood by the person skilled in the art. For instance, two cameras can be configured to receive light originating from the scanning focused light beam 5 according to the invention, while two other cameras can be configured to receive light originating from the diffuse light source 23.

As the optical properties of the inspected products can be wavelength dependent, inspection of the products can be done using a focused light beam 5 comprising light at different wavelengths. The camera 7 preferably is selected to be sensitive to more than one wavelength. The sensitivity of an inspection system according to this disclosure is primarily defined by the electromagnetic spectrum that can be sensed by the camera 7.

This scanning focused light beam 5 can originate from a single light source 16 providing electromagnetic radiation at different wavelengths. An example of such a single light source is a white laser typically providing light with a wavelength spectrum between 400 nm to 800 nm. Another example of such single light source is a supercontinuum laser capable of providing light with a wavelength spectrum between 400 nm and 2400 nm.

The scanning focused light beam can be created by combining light originating from several light sources 16, each light source providing electromagnetic radiation at one or more wavelengths or different wavelength spectra.

Preferably the scanning focused light beam 5 has a broad band power spectrum providing substantially the same power per wavelength or per wavelength spectral band. If that is not the case, corrections can be applied as is well known by a person skilled in the art.

There are applications however, such as in Raman spectroscopy, where it will be advantageous to have a concentrated light source with a very narrow spectral bandwidth and said concentrated light source, typically a laser, should in that case be selected appropriately as will be appreciated by the person skilled in the art.

The focused light beam 5 could allow for controlling the spot size of the light beam scanning the width of the product stream. This focused light beam 5 can comprise one or more laser beams. Alternatively the light source 16 generating the focused light beam 5 can be LED (light emitting devices) or halogen light bulbs combined with lenses creating a focused light beam.

In a preferred embodiment the focused light beam 5 scanning the product stream is generated by one or more laser sources 16 generating one or more laser beams which are incident on a rotating polygon mirror 17. Such a rotatable polygon mirror 17 has multiple facets along its sidewalls oriented towards the incoming laser beam. These facets of this mirror reflects the incident laser beam or laser beams towards the product stream, typically in a temporal saw tooth movement due the rotation of this mirror. An example of such a scanning focused light beam source 4 is disclosed in U.S. Pat. No. 6,509,537, hereby incorporated by reference, in particular in FIGS. 1 and 2 and corresponding paragraphs.

Upon illumination the scanned product 3 may reflect the incoming focused light beam in a characteristic spatial distribution, i.e. in a scattering and/or specular and/or diffuse way. Depending on its optical properties the scanned product 3 can also absorb, re-emit or transmit the incoming light 5. The returned light, i.e. wavelength, intensity, spatial distribution, is characteristic for the product 3, 3', 3" scanned.

The light 6 returned from the scanned product 3 is directly received by a camera 7 comprising at least one line of photosensitive elements or sensors. A line-scan camera only contains one line of sensors whereby the image of the scanned product is constructed by the successive read-out of line images taken. An area camera comprises an array of sensors, i.e. multiple lines of sensors, whereby the image of the scanned product is obtained by capturing the frame of the product. A sensor or group of sensors in the camera that can be individually addressed is labelled a pixel 9 as it constitutes the smallest element of the image taken that can be individually processed by the read-out circuitry.

Each pixel 9 in a line of sensors is allocated to a particular section $\Delta x_i$ in the direction x along the width W of the product stream. Each line of sensors in an array of sensors is allocated to a different section $\Delta y_i$ along the length of the product stream, i.e. the direction y along which the products are transported by the transport system 2. One single scan line creates a one-dimensional mapping of the irradiated energy related to every patch ($\Delta x_i$, $\Delta y_i$) of an observed camera line. A linear scan generates a line, showing on the y axis the irradiated energy of each patch ($\Delta x_i$, $\Delta y_i$) given in grey levels.

Depending on the configuration of the camera 7 a one-dimensional or two-dimensional image of the scanned product stream can be taken. Depending on the opto-electronic sensors used, one or more wavelengths can be detected by the camera 7. If multiple wavelengths can be detected, the spatial information registered for one wavelength can be combined with the spatial information registered for one or more other wavelengths.

Alternatively a camera 7 can be used that produces a two-dimensional image which contains in one dimension the spatial information and in the other dimension the spectral information for each spatial section $\Delta x_i$ along said direction x.

The opto-electrical sensors of the recording surface are selected to be sensitive to this returned light. Visible light can be detected by Si-based sensors such as photomultipliers, CMOS (drain junction diode) or CCD (charge coupled devices) camera's. Infrared light can be detected by different sensors each covering a part of the infrared light spectrum such as doped or undoped Si-based sensors, InGaAs-based sensors, InSb-based sensors, HgCdTe-based sensors, PbSe-based sensors as is known by a person skilled in the art.

The opto-electrical sensors can be selected from the range of sensors which are characterized in that they are internally arranged such that different regions on said sensor correspond with and are sensitive to different wavelengths. Such multi- or hyper-spectral imaging sensors are well-known in the art.

In general the camera will comprise an aperture allowing the returned light to enter the camera and a capturing surface for electronic recording of the light entering the camera. The size of the aperture and hence the amount of light entering the camera can be controlled using a diaphragm. The camera comprises one or more lenses and/or mirrors for collecting the returned light and for focusing the collected light onto the recording surface.

Additionally it may be required to use optical filters, such as bichroic mirrors, polarisers and such like in operable communication with said camera 7 in order to tune the spectral response of said camera according to the application requirements.

The recording sensors convert the optical signal into an electronic output signal. The smaller the size of the individually addressable pixels, the higher the resolution Rs (m) of the camera. The camera further comprises read-out circuitry for reading-out this electronic output signal. At each read-out of the camera, the converted optical signal of all individually addressable pixels is read-out thereby creating an image or frame of the scanned product stream.

Further handling of this electronic output signal can then be done by analog electrical circuitry or, after conversion into a digital signal, by digital signal processing circuitry.

Figure 9:
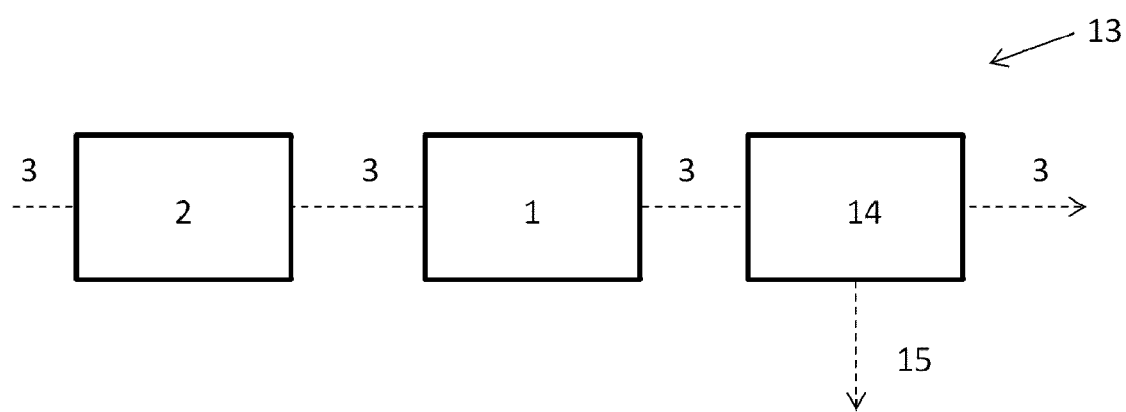
FIG. 9 illustrates the configuration of a sorting apparatus comprising an inspection system according to this disclosure.

An apparatus for inspecting products in a continuous way and for subsequently sorting of the inspected products is disclosed. Such sorting apparatus 13 comprises a transport system 2, an inspection system 1 according to any of the foregoing embodiments and a removal system 14 as illustrated in FIG. 9. The transport system 2 conveys the products 3 to be inspected in a single layer towards the inspection system 1 and the removal system 14. The inspection system 1 will analyze one or more predetermined characteristics of the conveyed products 3 individually. Typically optical characteristics such as wavelength(s) reflected or emitted (color), ratio of diffuse reflection to specular reflection and/or structure are being examined. Based upon the optical signals it receives, the inspection system 1 will evaluate if the measured values of these characteristics for a given product 3 in the product stream meet predetermined acceptance criteria. If not, this rejected product 15 is subsequently removed from the product stream 3 by the removal system 14. Hereto the inspection system 1 controls the operation of the removal system 14. When the decision is taken to remove certain products 15 from the product flow 3, a signal is given to the removal system 14. Typically this removal system 14 is a manifold of air pressure valves which can be opened on command. This allows the rejected element 15 to be blown out of the product stream 3 as soon as it enters the cone of high pressured air produced by such a valve, while the accepted elements continue their movement.

Other embodiments to inspect and/or sort a stream of products can be envisaged. For instance an apparatus where said inspection system is moved along the stream of products while said stream of products remains static.

The sorting apparatus 13 can be operated as follows. Products 3, 3', 3" are provided by the transport system 2. The inspection system 1 continuously scans the product stream in a direction x substantially perpendicular to the direction y in which the products are moved forward by the transport system 2. At the start of taking a new image, a start signal is generated indicative of the start of a new scan, i.e. one sweep of the focused light beam 5 over the width of the product stream. This start signal triggers the camera 7 of the inspection system 1 to detect the light 6 directly returned from the scanned products 3. While the product stream is being continuously scanned, the camera 7 records the optical information provided at least by light 6 originating directly from the scanned products 3. When the total scan time corresponding to an integer number of successive scans is equal to the selected exposure time of the camera 7, the camera 7 stops detecting the returned light 6 and the image is ready for read-out and further analysis. The start signal of the next scan then triggers the recording of the next image. As the length of the exposure time for an image of the product stream is synchronized with the number of scans over the product stream performed by the focused light beam 5, each position along the scan line will be illuminated with substantially the same accumulated light energy provided by the focused light beam 6. The above corresponds to the case where the exposure time $T_e$ of the camera (the taking of one image) is an integer multiple of the scan time Tw, hence Te=n×Tw with n higher than or equal to 1. A more preferred case is the one where n is equal to or higher than 2, for reasons of signal to noise ratio, explained above. In both cases (n≥1 and n≥2), the camera may take multiple images taken over multiple exposure times, which are read out and added together in the camera or in a processing device outside the camera. In a more general case, the exposure time is chosen so that K×Te equals L×Tw with L and K integers higher than or equal to 1. In that case, when the total exposure time equals an integer number K of exposure times $T_e$, the camera is instructed to stop detecting the returned light at the end of the period $L*T_w$, which is equal to $K*T_e$, and the subsequent K images are integrated (added) in the camera or in a processing device separate from the camera. The most general case is the one where the exposure time Te is an integer ratio n/m of the scan time, wherein the exposure time is started upon receiving a signal that the scanning is initiated, and wherein after detecting that an integer number of scan times have been applied, the data obtained during the exposure time is read out and processed. In this case, one exposure time may correspond for example to 1.5 time the scan time (as in the example explained elsewhere in this description). Even though not all the points in the detection area have then received the same amount of light during the exposure time, the knowledge that one half of the points have obtained twice the amount of the other half, allows the processing means to analyse the data taking this knowledge into account.

The start of the next frame can coincide with the stop of the previous frame. Alternatively there could be a certain period in between the stop of the previous frame and the start of the next frame in which the camera is not recording. Such a situation may require a stop signal in addition to a start signal.

The inspection system 1 according to the first aspect can be applied in different types of sorting apparatus as illustrated by FIG. 9. The products 3 can be transported by e.g. a conveyor belt, a vibration table, a shaker and such like. The products 3 can be inspected while on the transport system 2, e.g. when being on a conveyor belt, or when moving between the transport system 2 and the removal system 14, e.g. when being propelled into the air by conveyor belt in the case of free flight sorting apparatus or e.g. after being guided into a free fall trajectory by a chute in the case of a free fall sorting apparatus.

The invention is applicable to a number of existing types of sorting apparatus. For example, U.S. Pat. No. 6,509,537, hereby incorporated by reference, discloses in FIG. 1 and corresponding paragraphs a sorting apparatus wherein the transport system 2 is a conveyor belt. The products 3 in the product stream are scanned when transported by this conveyor belt. The light directly returned by the scanned products can be detected by a camera 7 whereby the total scan time is synchronized with the exposure time of this camera 7 in accordance with the disclosure of the first aspect of the present invention.

EP patent application EP 1 726 372, hereby incorporated by reference, discloses in particular in FIG. 1 and FIG. 3 and corresponding paragraphs a sorting apparatus wherein the transport system is a vibration table supplying the products to a chute guiding the products 3 to the inspection system 1. In FIG. 1 a sorting apparatus having one inspection system is shown scanning the front side of the product stream, whereas in FIG. 2 two inspection systems are shown scanning respectively the front and rear side of the product stream. The scanning movement of both scanning light beams is correlated to prevent products being scanned by both lasers at the same time. The light directly returned by the scanned products can be detected by a camera 7 whereby the total scan time is synchronized with the exposure time of this camera 7 in accordance with the disclosure of the first aspect of the invention.

Figure 10:
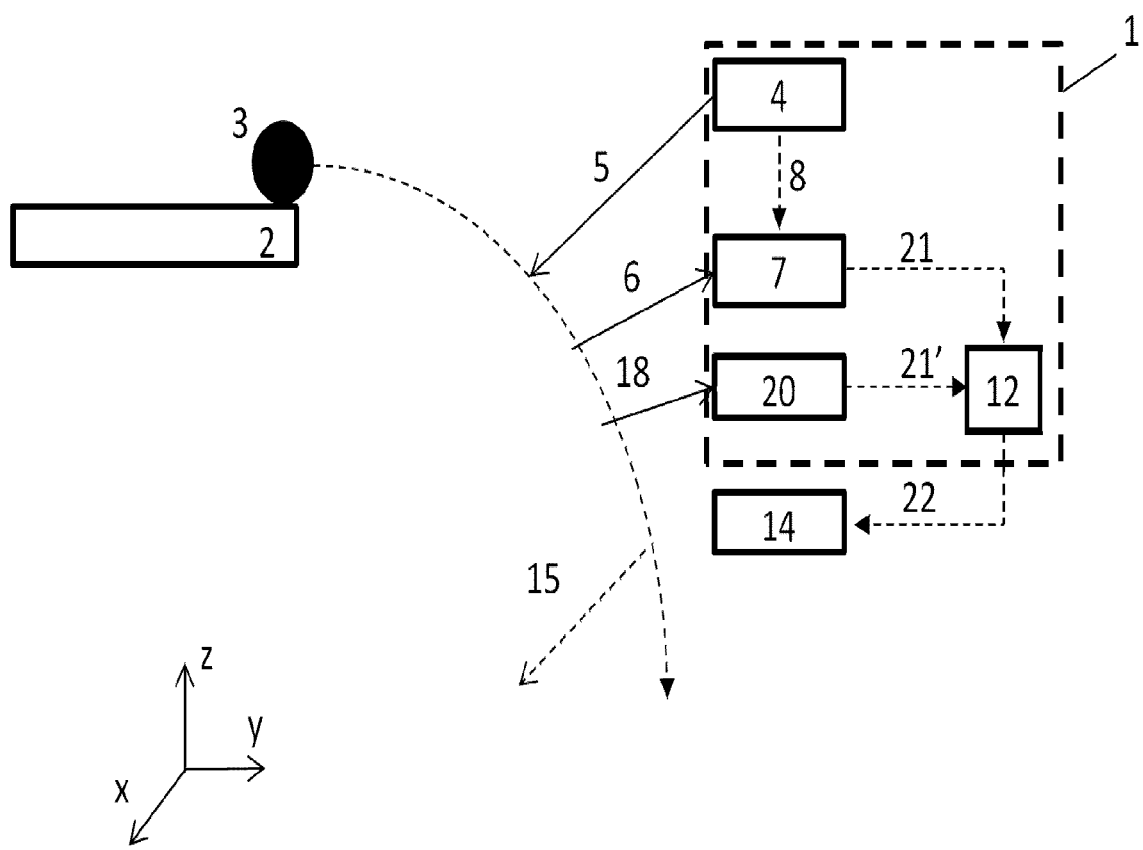
FIG. 10 illustrates a sorting apparatus comprising an inspection system according to this disclosure.

FIG. 10 illustrates a free flight sorting apparatus comprising an inspection system 1 according to this disclosure. Products 3 are provided to the inspection system 1 by the transport system 2 for analysis thereof towards the inspection system 1. These products can be guided into a free fall trajectory using a chute (not shown). The inspection system 1 comprises a first inspection unit which comprises a source 4 of a scanning focused light beam 5 and a camera 7. As discussed in the first aspect the scanning movement of the focused light beam 5 is synchronized 8 with the exposure time of the camera 7 to minimize or even prevent differences in total illumination time or illumination dose between the products 3 scanned. Camera 7 can take 6 an image of the product stream for further spectral or spatial analysis 21 thereof. A control unit 12 can instruct 22 the removal system 14 to reject a product 15 that doesn't meet the acceptance criteria.

In addition to the camera 7, the inspection system 1 further comprises a detector 20 receiving light 18 returned from the product stream via a polygonal mirror 17 (not shown). This detector allows analysing the spatial distribution, i.e. scattering or specular or diffuse reflection of the incoming scanning focused light beam 5. Based on the analysis 21' of the detected returned light 18, a control unit 12 can instruct 22 the removal system 14 to reject a product 15 that doesn't meet the acceptance criteria.

Whereas in the inspection system 1 illustrated by FIG. 6 the same light source 16 is used to generate the returned light beams 18 and 6, here the focused light beam 5 generating the returned light 18 can be generated by a scanning light source other than the scanning light source used for generating the light 6 directly returned to the camera 7.

Light returned by a product 3 along its trajectory is hence detected and analysed 21, 21' by both the camera 7 and the detector 20. The order in which this dual analysis is performed can be chosen. The optical information originating from this product 3 either detected by the camera 7 and/or by the detector 20 is analysed to check if the product meets the acceptance criteria. By combining the optical information 6, 18 from both 7,20 a more complete analysis of each product 3 is obtained in order to instruct 22 the removal system 14 to remove 15 or retain the inspected product 3. Combining signals includes but is not limited to comparing, adding, subtracting, multiplying or dividing two or more of said signals 6,18 or any algebraic combination thereof.

The present invention is not limited to embodiments that synchronize, or methods that require synchronization of, the exposure time $T_e$ up to a theoretically exact integer multiple of the scan time $T_w$ or to an exact integer ratio of T. The person skilled in the art will understand that certain tolerances on the integer ratio of $T_w$ by $T_e$ are still within the scope of this invention. It would be immediately understood that the synchronization accuracy should only be such that like objects produce like results. The person skilled in the art would therefore fully appreciate that the exposure time $T_e$ should only be substantially equal to an integer ratio of the scan time $T_w$.

The invention claimed is:

1. An inspection system (1) for individually analyzing products (3) transported in a continuous stream, the system comprising a scanning focused light (5) beam source (4), configured to scan the width (W) of the product stream in a period of time referred to as the scan time (Tw), the width (W) being the linear direction of the product stream in a direction x substantially perpendicular to the direction y along which the product stream is transported, a camera (7) positioned to detect light beams (6) directly returned from the scanned product stream during a period of time referred to as the exposure time (Te) of the camera, thereby providing an image of the scanned product stream, and a control unit (12) configured to synchronize the scanning of the focused light beam (5) with the exposure time of the camera (7), wherein synchronizing comprises configuring the exposure time and the scan time so that the exposure time (Te) is substantially equal to an integer ratio of the scan time (Tw), i.e. Te is substantially equal to (n/m)×Tw with n and m integers equal to or higher than 1.

2. The inspection system according to claim 1, wherein the exposure time Te is substantially equal to an integer multiple of the scan time, i.e. Te is substantially equal to n×Tw, with n an integer equal to or higher than 1.

3. The inspection system according to claim 2, wherein n is an integer equal to or higher than 2.

4. The inspection system (1) according to claim 1, further comprising a start sensor (10) and stop sensor (11) positioned with respect to the light source (4) to define the angle over which the focused light beam (5) moves when scanning the product stream (3), whereby the start sensor (10) and the stop sensor (11) are configured to provide a control signal (8) to the control unit (12) indicative of respectively the start and the stop of a scan movement of the focused light beam (5).

5. The inspection system (1) according to claim 1, further comprising a start sensor (10) positioned with respect to the light source (4) to define the angle over which the focused light beam (5) moves when scanning the product stream (3), whereby the start sensor (10) is configured to provide a control signal (8) to the control unit (12) indicative of both the start and the stop of a scan movement of the focused light beam (5).

6. A method for operating an inspection system (1) for individually analyzing products (3) transported in a continuous stream, the system comprising a scanning focused light (5) beam source (4), configured to scan the width (W) of the product stream in a period of time referred to as the scan time (Tw), the width (W) being the linear dimension of the product stream in a direction x substantially perpendicular to the direction y along which the product stream is transported, a camera (7) positioned to detect light beams (6) directly returned from the scanned product stream during a period of time referred to as the exposure time (Te) of the camera, thereby providing an image of the scanned product stream, and a control unit (12) configured to synchronize the scanning of the focused light beam (5) with the exposure time of the camera (7), the method comprising:
  initiating scanning of the product stream (3) thereby generating a signal (8) to the control unit (12) to start recording the number of scans being performed and to the camera (7) to start integrating the light returned by the scanned products (6) towards the camera (7),
  checking if the number of scans performed corresponds to a preset integer multiple of the scan time (Tw), and
  if yes, processing the image or images taken, wherein the exposure time (Te) is substantially equal to an integer ratio of the scan time (Tw), i.e. Te=(n/m)×Tw with n and m integers equal to or higher than 1.

7. Method according to claim 6, comprising the steps of:
  initiating scanning of the product stream (3) thereby generating a signal (8) to the control unit (12) to start recording the number of scans being performed and to the camera (7) to start integrating the light returned by the scanned products (6) towards the camera (7), during one or more exposure times (Te),
  checking if the number of scans performed corresponds to a preset integer multiple L of the scan time (Tw), i.e. the total scan time is substantially equal to L×Tw with L an integer equal to or higher than 1, and
  if yes, instructing the camera (7) to stop detecting the returned light (6) and processing the image or images taken, wherein the exposure time (Te) is chosen so that the total exposure time when the detection is stopped is substantially equal to a integer multiple of said exposure time, i.e. total exposure time substantially equals K×Te with K equal to or higher than 1, so that K×Te substantially equals L×Tw.

8. Method according to claim 6, wherein the exposure time Te is substantially equal to an integer multiple of the scan time, i.e. Te is substantially equal to n×Tw, with n an integer equal to or higher than 1.

9. Method according to claim 7, wherein the exposure time Te is substantially equal to an integer multiple of the scan time, i.e. Te is substantially equal to n×Tw, with n an integer equal to or higher than 1.

10. Method according to claim 8, wherein n is an integer equal to or higher than 2.

11. An apparatus for sorting products (13), comprising a transport system (2) configured to supply the products (3) in a continuous single layer stream to an inspection system (1) which is positioned towards the product stream (3) to allow analysis of individual products and a removal system (14) operatively coupled to the inspection system to remove products (15) analyzed by the inspection system (1), wherein the inspection system (1) is according to claim 1.

12. A method for operating the sorting apparatus (13) according to claim 11, comprising
  providing the product stream (3),
  initiating scanning of the product stream (3) thereby generating a signal (8) to the control unit (12) to start recording the number of scans being performed and to the camera (7) to start integrating the light returned by the scanned products (3) towards the camera (7),
  checking if the number of scans performed corresponds to an integer multiple of the scan time (Tw),
  if yes, processing the image or images taken, wherein the exposure time (Te) is substantially equal to an integer ratio of the scan time (Tw), i.e. Te is substantially equal to (n/m)×Tw with n and m integers equal to or higher than 1, and
  on the basis of said processing, analysing and if necessary removing individual products from said product stream.

13. Method according to claim 12, comprising the steps of:
  initiating scanning of the product stream (3) thereby generating a signal (8) to the control unit (12) to start recording the number of scans being performed and to the camera (7) to start integrating the light returned by the scanned products (6) towards the camera (7), during one or more exposure times (Te),
  checking if the number of scans performed corresponds to a preset integer multiple L of the scan time (Tw), i.e. the total scan time is equal to L×Tw with L an integer equal to or higher than 1, and
  if yes, instructing the camera (7) to stop detecting the returned light (6) and processing the image or images taken, wherein the exposure time (Te) is chosen so that the total exposure time when the detection is stopped is a integer multiple of said exposure time, i.e. total exposure time equals K×Te with K equal to or higher than 1, so that K×Te substantially equals L×Tw
  on the basis of said processing, analysing and if necessary removing individual products from said product stream.

14. Method according to claim 12, wherein the exposure time Te is an integer multiple of the scan time, i.e. Te is substantially equal to n×Tw, with n an integer equal to or higher than 1.

15. Method according to claim 14, wherein n is an integer equal to or higher than 2.

16. The inspection system according to claim 1, wherein the focused light beam (5) is moved from one side of the product stream to an opposite side of the products stream during the scan time (Tw) to scan the width (W).

17. The inspection system according to claim 16, wherein the spot size of the focused light beam (5), at least along the width, is less than the width (W).

18. The method according to claim 6, wherein the focused light beam (5) is moved from one side of the product stream to an opposite side of the products stream during the scan time (Tw) to scan the width (W).

19. The method according to claim 18, wherein the spot size of the focused light beam (5), at least along the width, is less than the width (W).

* * * * *